United States Patent
Hofmann et al.

(10) Patent No.: US 8,088,426 B2
(45) Date of Patent: *Jan. 3, 2012

(54) KOKUMI FLAVOUR COMPOUNDS AND USE

(76) Inventors: Thomas Frank Hofmann, Neufahrn (DE); Andreas Dunkel, Freising (DE)

(*) Notice: Subject to any disclaimer, the term of this patent is extended or adjusted under 35 U.S.C. 154(b) by 844 days.

This patent is subject to a terminal disclaimer.

(21) Appl. No.: 12/089,653

(22) PCT Filed: Oct. 11, 2006

(86) PCT No.: PCT/EP2006/009839
§ 371 (c)(1),
(2), (4) Date: May 20, 2008

(87) PCT Pub. No.: WO2007/042288
PCT Pub. Date: Apr. 19, 2007

(65) Prior Publication Data
US 2009/0130282 A1  May 21, 2009

(30) Foreign Application Priority Data
Oct. 14, 2005 (GB) .................................. 0520912.7

(51) Int. Cl.
*A23L 1/22* (2006.01)
(52) U.S. Cl. .......... 426/533; 426/534; 426/535; 426/650
(58) Field of Classification Search .................. 426/533, 426/534, 535, 650
See application file for complete search history.

(56) References Cited

FOREIGN PATENT DOCUMENTS

| | | |
|---|---|---|
| EP | 0672354 A1 | 9/1995 |
| GB | 1560000 A | 1/1980 |
| JP | 52007468 A | 1/1977 |
| WO | 02/087361 A | 11/2002 |

OTHER PUBLICATIONS

English Language Abstract for JP52007468 taken from Westlaw.

*Primary Examiner* — Leslie Wong
(74) *Attorney, Agent, or Firm* — Norris McLaughlin & Marcus PA

(57) ABSTRACT

The invention relates to compounds of formula (I) that provide a kokumi flavor to consumables and flavor compositions, and to consumables and flavor compositions comprising such compounds. Enzymatic methods to prepare the compounds are provided.

19 Claims, No Drawings

KOKUMI FLAVOUR COMPOUNDS AND USE

This is an application filed under 35 USC 371 of PCT/EP2006/009839.

This invention relates to the use of kokumi flavourant compounds in consumables, and to flavour compositions comprising such compounds.

"Kokumi" is a term used in the flavour industry to describe characteristics such as continuity, mouthfulness, richness and thickness. In contrast thereto, the sensory terms for the basic tastes are salty, sweet, sour, bitter or umami, the last-named being the taste of monosodium glutamate (MSG). Kokumi is a distinct taste quality, or rather a taste-enhancing quality, which can be easily detected and differentiated by sensory tests by a trained panel. Compounds that provide a kokumi taste are usually tasteless in water, but enhance the taste in combination with other tastants in respect of the above-mentioned qualities.

In addition to the desired organoleptic properties, compounds should preferably have one or more of the following characteristics: they should be inexpensive to produce, stable during long periods of storage and to processing conditions that may comprise elevated temperatures and humidity, and extremes of pH.

Applicant identified compounds according to formula I that belong to the group of esters of S- or O-carboxyalkylated gamma-glutamyl and beta-asparagyl peptides which are able to provide a "kokumi" flavour to consumables and fulfill the above requirements.

Whereas no literature information is available on sensory properties of beta-asparagyl peptides, certain gamma-glutamyl peptides are known to provide or change flavour properties. Gamma L glutamyl dipeptide-derivates of Phe, Val, Leu and His are known to reduce the bitterness of the original amino acids (Phe, Val, Leu, His) (Suzuki et al., J. Agric. Food Chem. 2002, 50, 313-318).

Various sulfur-containing peptides including alliin ((+)-S-allyl-L-cysteine sulfoxide), cycloalliin ((3-(S)-methyl-1,4-thiazane-5-(R)-carboxylic acid 1-oxide), MeCSO ((+)-S-methyl-L-cysteine sulfoxide), GACSO, (gamma-L-glutamyl-S-allyl-L-cysteine sulfoxide), GAC (gamma-L-glutamyl-5-allyl-L-cysteine sulfoxide), and GSH (Glutathione, Gamma-L-glutamyl-L-cysteinyl-glycine or γ-Glu-Cys-Gly) are known to impart a "kokumi" taste to aqueous umami solutions containing monosodium glutamate (MSG) and ribonucleotides or to an aqueous model beef extract (Ueda et al. Agric. Biol. Chem. 1990, 54, 163-169; Ueda et al., Biosci. Biotech. Biochem. 1997, 61, 1977-1980). GSH and other compounds containing free SH groups are less stable as they tend to form disulfites which provide a less intensive kokumi taste and as they can react with compounds present in flavour compositions or consumables. Further, GSH reacts acidic when added to aqueous solutions and the flavour composition or consumable needs to be adjusted in pH accordingly.

There remains a need for alternative or improved compounds to provide a "kokumi" taste to consumables.

Surprisingly, applicant has identified very stable compounds formula I that are able to provide a kokumi taste and do not significantly alter the pH of aqueous solutions. This was entirely unpredictable from the prior art.

In a first aspect, the invention is therefore directed to the use as a flavour of a compound of formula I, or a salt thereof,

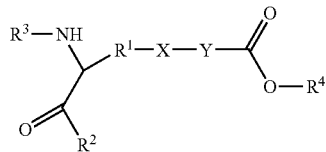

wherein the residues $R^1$, $R^2$, $R^3$, $R^4$, X and Y are selected as follows:

$R^1$ is a residue selected from $-CH_2-$; $-CH_2CH_2-$ or $-CH_2CH_2CH_2-$;

$R^2$ is a residue selected from $-OH$, $-C_1-C_5$ linear or branched alkoxy residue including $-O-CH_3$, $-O-CH_2-CH_3$, $-O-CH_2CH_2CH_3$, $-O-CH(CH_3)CH_3$, $-O-CH_2CH(CH_3)_2$, $-O-CH_2CH(CH_3)(CH_2CH_3)$, and $-O-CH_2CH_2CH(CH_3)_2$ and the residue of an amino acid selected from the group consisting of α-Ala, α-Gly, α-Val, α-Leu, α-Ile, α-Met, α-Pro, α-Phe, α-Trp, α-Ser, α-Thr, α-Asn, α-Gln, α-Tyr, α-Cys, α-Lys, α-Arg, α-His, α-Asp, α-Glu, β-Ala, and gamma amino butyric acid (GABA), and an uncommon amino acid including 4-hydroxyprolin, ε-N,N,N-trimethyllysine, 3-methylhistindine, 5-hydroxylysine, O-phosphoserine, gamma-carboxyglutamate, ε-N-acetyllysine, ω-N-methylarginine, N-acetylserine, N,N,N-trimethylalanine, N-formylmethionine;

$R^3$ is a residue selected from the group of a residue of γ-Glu $(-CO-CH_2-CH_2-CH(NH_2)-COOH)$, and β-Asp $(-CO-CH_2-CH(NH_2)-COOH)$;

X is a residue selected from $-S-$ or $-O-$; and

Y is a residue selected from the group consisting of $-CH_2-$, $-CH_2CH_2-$, $-CH_2CH_2CH_2-$, $-CH(COOR^4)-$, $-C(COOR^4)_2-$, $-C(CH_2COOR^4)_2-$, $-C(CH_2COOR^4)(COOR^4)-$, $-C(CH(COOR^4)_2)(COOR^4)-$, $-CH(CH_2COOR^4)-$, $-CH(CH_2CH_2COOR^4)-$, $-CH(CH_2CH_2CH_2COOR^4)-$, $-CH(CH(COOR^4)_2)-$, $-CH(CH(COOR^4)CH(COOR^4)_2)-$, $-CH(CH_2CH(COOR^4)_2)-$, $-CH(CH(COOR^4)CH_2COOR^4)-$, $-CH_2-CH(COOR^4)-$, $-CH_2-C(COOR^4)_2-$, $-CH_2-C(CH_2COOR^4)_2-$, $-CH_2-C(CH_2COOR^4)(COOR^4)-$, $-CH_2-C(CH(COOR^4)_2)(COOR^4)-$, $-CH_2-CH(CH_2COOR^4)-$, $-CH_2-CH(CH_2CH_2COOR^4)-$, $-CH_2-CH(CH_2CH_2CH_2COOR^4)-$, $-CH_2-CH(CH(COOR^4)_2)-$, $-CH_2-CH(CH(COOR^4)CH(COOR^4)_2)-$, $-CH_2-CH(CH_2CH(COOR^4)_2)-$, $-CH_2-CH(CH(COOR^4)CH_2COOR^4)-$, $-CH(COOR^4)-CH_2-$, $-C(COOR^4)_2-CH_2-$, $-C(CH_2COOR^4)_2-CH_2-$, $-C(CH_2COOR^4)(COOR^4)-CH_2-$, $-C(CH(COOR^4)_2)(COOR^4)-CH_2-$, $-CH(CH_2COOR^4)-CH_2-$, $-CH(CH_2CH_2COOR^4)-CH_2-$, $-CH(CH_2CH_2CH_2COOR^4)-CH_2-$, $-CH(CH(COOR^4)_2)-CH_2-$, $-CH(CH(COOR^4)CH(COOR^4)_2)-CH_2-$, $-CH(CH(COOR^4)CH_2COOR^4)-CH_2-$; and $R^4$ is a residue selected from a $C_1-C_5$ linear or branched alkyl residue including $-CH_3$, $-CH_2-CH_3$, $-CH_2CH_2CH_3$, $-CH(CH_3)CH_3$, $-CH_2CH(CH_3)_2$, $-CH_2CH(CH_3)(CH_2CH_3)$, and $-CH_2CH_2CH(CH_3)_2$, and wherein individual $R^4$ residues are chosen independently of each other, and wherein, when more than two $R^4$ residues are present, at least one $R^4$ residue is a $C_1$-$C_5$ linear or branched alkyl residue and of the remaining $R^4$ residues, one or more may be H, and wherein, when one of the $R^4$ residues is a propyl, butyl or pentyl residue, then the other $R^4$ residues are selected from methyl or ethyl or H.

Standard abbreviations for amino acids are used throughout this text to identify their residues within a larger compound rather than the free amino acid, for example $R^3$ above may be a residue of γ-Glu or β-Asp.

A compound of formula I may be present in the form as shown or in its ionic form with a counter-ion (in form of its salt), for example its sodium, potassium, calcium, ammonium, chloride, sulfate, phosphate, carbonate salt, or similar.

In another aspect, the invention is directed to the use of a compound of formula I wherein two or more identical $R^4$ residues are present.

In another aspect, the invention is directed to the use of a compound of formula I wherein R1 is selected from —CH$_2$— and —CH$_2$CH$_2$.

In another aspect, the invention is directed to the use of a compound of formula I wherein $R^1$ is —CH$_2$— und —CH$_2$CH$_2$.

In another aspect, the invention is directed to the use of a compound of formula I wherein $R^3$ is γ-Glu.

In another aspect, the invention is directed to the use of a compound of formula I wherein $R^4$ is selected from —CH$_3$, and —CH$_2$—CH$_3$.

In another aspect, the invention is directed to the use of a compound of formula I wherein X is S.

In another aspect, the invention is directed to the use of a compound of formula I wherein Y is selected from the group consisting of —CH$_2$—, —CH(COOR$^4$)—, —CH(COOR$^4$)CH$_2$—, —CH(CH(COOR$^4$)$_2$)—, —CH$_2$CH$_2$—, —CH$_2$CH$_2$ CH$_2$—, and —CH(CH$_2$COOR$^4$)CH$_2$.

In another aspect, the invention is directed to the use of a compound of formula I wherein $R^3$ is γ-Glu, and $R^4$ is selected from —CH$_3$, and —CH$_2$—CH$_3$.

In another aspect, the invention is directed to the use of a compound of formula I wherein $R^3$ is γ-Glu, and X is S.

In another aspect, the invention is directed to the use of a compound of formula I wherein $R^3$ is γ-Glu, and Y is selected from the group consisting of —CH$_2$—, —CH(COOR$^4$)—, —CH(COOR$^4$)CH$_2$—, —CH(CH(COOR$^4$)$_2$)$_n$—CH$_2$CH$_2$—, —CH$_2$CH$_2$ CH$_2$—, and —CH(CH$_2$COOR$^4$)CH$_2$.

In another aspect, the invention is directed to the use of a compound of formula I wherein $R^3$ is γ-Glu, $R^4$ is selected from —CH$_3$, and —CH$_2$—CH$_3$, X is S, and Y is selected from the group consisting of —CH$_2$—, —CH(COOR$^4$)—, —CH(COOR$^4$)CH$_2$—, —CH(CH(COOR$^4$)$_2$)—, —CH$_2$CH$_2$—, —CH$_2$CH$_2$ CH$_2$—, and —CH(CH$_2$COOR$^4$)CH$_2$.

In another aspect, the invention is directed to the use of a compound of formula I wherein more than two $R^4$ residues are present, and at least one $R^4$ residue is a $C_1$-$C_5$ linear or branched alkyl residue and of the remaining $R^4$ residue or residues, one or more is H.

In another aspect, the invention is directed to the use of a compound of formula I wherein more than two $R^4$ residues are present, and at least one $R^4$ residue is a $C_1$-$C_5$ linear or branched alkyl residue and of the remaining $R^4$ residue or residues, two or more are H.

The use of compounds wherein more than two $R^4$ residues are present, and at least one $R^4$ residue is a $C_1$-$C_5$ linear or branched alkyl residue and of the remaining $R^4$ residue or residues, one or more is H will provide, in addition to the kokumi taste, a salt enhancement that is more pronounced for $R^4$ with at least two H residues. These compounds provide salt-enhancing properties in compositions and consumables. By salt, NaCl and or KCl, or the corresponding dissociated ions are meant. The compounds of formula I enhance the salt taste whereby the taste of the salt that is present is rendered more noticeable, and either the consumable tastes more salty, or the salt concentration can be reduced to provide the same degree of saltiness (isosaltiness) at a reduced NaCl and/or KCl concentration. The degree of enhancement in consumables may be, for example, an additional 25% up to 100% (saltiness is doubled), or 200% or more. Accordingly, it is possible to reduce the sodium content by more than half (+100%) and achieve the same saltiness (or even more if KCl is employed).

By the addition of said salt-enhancing compounds, consumables moderate, reduced or low in sodium or salt may be formed (sodium concentrations are given below. To calculate salt content, multiply by 2.5). 250 mg to 1250 mg per 100 g or ml sodium is usually considered a moderate amount, while consumables above 1250 mg per 100 g or ml is considered a high amount. 0 to 250 mg/100 g or ml can be considered a low amount.

Consumables according to the invention may, for example, have the following sodium concentrations: 5 to 1250 mg/100 g or ml, 5 to 600 mg/100 g or ml, 5 to 250 mg/100 g or ml, 5 to 200 mg/100 g or ml, 5 to 140 mg/100 g or ml, 5 to 100 mg/100 g or ml, or 5 to 40 mg/100 g or ml. While 5 mg is a useful minimum sodium concentration, if less saltiness is to be achieved, the lower concentration may be even lower, for example 4, 3, 2, or 1 mg/100 g or 100 ml. Furthermore, if a very high degree of saltiness is to be achieved, a higher salt content may be chosen.

Examples of subgroups of these useful groups are listed below with residues $R^1$-$R^4$, X and Y. These provide a very good kokumi activity.

|   | $R^1$ | $R^2$ | $R^3$ | $R^4$ | X | Y |
|---|---|---|---|---|---|---|
| 1 | CH$_2$ | OH, Gly, βAla, OCH$_3$, OC$_2$H$_5$ | γ-Glu | —CH$_3$, —CH$_2$—CH$_3$ | S | CH(COOH) |
| 2 | CH$_2$CH$_2$ | OH, Gly, βAla, OCH$_3$, OC$_2$H$_5$ | γ-Glu | —CH$_3$, —CH$_2$—CH$_3$ | S | CH(COOH) |
| 3 | CH$_2$ | OH, Gly, βAla, OCH$_3$, OC$_2$H$_5$ | γ-Glu | —CH$_3$, —CH$_2$—CH$_3$ | S | CH(COOH)CH$_2$ |
| 4 | CH$_2$CH$_2$ | OH, Gly, βAla, OCH$_3$, OC$_2$H$_5$ | γ-Glu | —CH$_3$, —CH$_2$—CH$_3$ | S | CH(COOH)CH$_2$ |
| 5 | CH$_2$ | OH, Gly, βAla, OCH$_3$, OC$_2$H$_5$ | γ-Glu | —CH$_3$, —CH$_2$—CH$_3$ | S | CH(CH$_2$COOH)CH$_2$ |
| 6 | CH$_2$CH$_2$ | OH, Gly, βAla, OCH$_3$, OC$_2$H$_5$ | γ-Glu | —CH$_3$, —CH$_2$—CH$_3$ | S | CH(CH$_2$COOH)CH$_2$ |

-continued

| R¹ | R² | R³ | R⁴ | X | Y |
|---|---|---|---|---|---|
| 7 CH₂ | OH, Gly, βAla, OCH₃, OC₂H₅ | γ-Glu | —CH₃, —CH₂—CH₃ | S | CH(CH₂CH₂COOH) |
| 8 CH₂CH₂ | OH, Gly, βAla, OCH₃, OC₂H₅ | γ-Glu | —CH₃, —CH₂—CH₃ | S | CH(CH₂CH₂COOH) |

In another aspect, the invention is directed to flavour compositions comprising one or more compounds of formula I as hereinabove defined.

In another aspect, the invention is directed to consumables comprising one or more compounds of formula I as hereinabove defined, or mixtures thereof, in a concentration of 1 to 25.000 ppm (weight/weight).

An appropriate concentration in which to employ compounds will depend on the type of consumable and the desired taste intensity. For example, compounds according to the invention may be employed at a concentration of, for example, 1 to 10,000 ppm, 5 to 25,000 ppm, 10 to 10,000 ppm, 50 to 5000 ppm, and 100 to 1000 ppm (based on weight).

Compounds of formula I have not been described previously. Accordingly, in another aspect, the invention is directed to compounds of formula I as hereinabove described.

In another aspect, the invention is directed to a method for imparting a kokumi taste to a consumable, comprising the addition of a compound as hereinabove described to a consumable. The compound may be added in the form of an unpurified enzymatic reaction mixture in which it was formed, in the form of a crude extract of such a mixture, in the form of a plant extract, or in purified form.

Compounds for use in the present invention may be prepared according to procedures well known in the art.

Certain γ-glutamyl dipeptides of formula I can also be prepared enzymatically using gamma-glutamyl-transpeptidase enzyme (GGTP) as is well known in the art using enzymes from various sourcex including commercial sources and described previously, for example, by Suzuki et al., J. Mol. Catal. 1999, B6, 175-184; Suzuki et al., J. Agric. Food Chem. 2002, 50, 313-318), Suzuki et al.; J. Agric. Food Chem.; 52 (2004); 577-580; Strumeyer and Bloch, Biochem. Prep. 1962, 9, 52-55; Thompson and Meister, Proc. Nat. Acad. Sci. USA, 1975, 72, 1985-1988; Allison and Meister, J. Biol. Chem. 1981, 256, 2988-2992; Meister, The Enzymes B (Academi, New York), 3rd. Ed., Vol. 10, pp. 671-697; Strumeyer and Bloch, J. Biol. Chem. 1969, 235, 27; Thompson and Meister, Proc. Nat. Acad. Sci. USA, 1975, 72, 1985-1988; Oppenheimer et al., J. Biol. Chem. 1979, 254, 5184-5190; Tate and Meister, J. Biol. Chem., 1975, 250, 4619-4627.

Starting materials and the enzymes are readily available commercially or can be obtained as described in the references indicated above.

Another possibility is the chemical synthesis of peptides from amino acids which is well-known in the art. Non-natural amino acids can be formed by introducing side chains as desired and this also is well-known in the art. The peptide ester component of the compounds may be synthesised as will be apparent to the skilled person, or purchased commercially.

In another aspect the invention is directed to a method of forming a novel compound of formula I as hereinabove defined by chemical or enzymatical synthesis.

The formed products may be purified and used as a flavour in purified form, or they may be used as a flavour in crude form (enzymatic reaction mixture) or as a crude extract from fermentation or from enzymatic reaction with the isolated enzyme.

If so desired, the product may be purified as follows: lyophilisation, followed by chromatographic work-up, for example gel permeation chromatography may be employed. Chromatography may be performed, for example, with Sephadex G-10 (Amersham Bioscience, Uppsalla, Sweden) as stationary and water as mobile phase. The effluent is monitored, for example using an UV-detector at 220 nm. The product eluate can be confirmed by analytical methods well-known in the art, for example by liquid chromatography and mass spectrometry (LC-MS) and nuclear magnetic resonance (NMR) spectroscopy.

A compound for use in the present invention imparts a kokumi taste to consumables. Consumables as used herein include food products, beverages, oral care products, and compositions for admixture to such products, in particular flavour compositions. Flavour compositions may be added to processed foods or beverages during their processing, or they may actually be consumables in their own right, e.g. condiments such as sauces and the like.

A compound of the present invention or a mixture thereof may be used as a flavour ingredient in flavour compositions. A compound or mixture of compounds may be blended with other flavour ingredients in said compositions. A compound or mixture of compounds imparts a kokumi taste to all kinds of consumables, and is particularly interesting in savoury consumables.

Examples of consumables include cereal products, baker's products, bread products, gums, chewing gums, yeast products, salt and spice products, mustard products, vinegar products, sauces (condiments), soups, processed foods, cooked fruits and vegetable products, meat and meat products, egg products, milk and dairy products, cheese products, butter and butter substitute products, milk substitute products, soy products, edible oils and fat products, medicaments, beverages, alcoholic drinks, beers, soft drinks, food extracts, plant extracts, meat extracts, condiments, sweeteners, nutraceuticals, pharmaceutical and non-pharmaceutical gums, tablets, lozenges, drops, emulsions, elixirs, syrups and other preparations for making beverages, instant beverages and effervescent tablets.

The flavourant qualities of compounds of the formula I may be evident over a broad range of concentrations. For example, in the case of a food or beverage product, a compound or mixture of compounds may be present in a concentration ranging from, for example, 1 to 10,000 ppm, 5 to 25,000 ppm, 10 to 10,000 ppm, 50 to 5000 ppm, and 100 to 1000 ppm (based on weight). The skilled person will appreciate that the appropriate concentration will depend on the consumable, the presence of other flavours, and the desired flavour intensity. The concentration can easily be adjusted by the skilled person to the desired effect.

A person skilled in the art will appreciate that formulations and consumables may contain additional ingredients which may comprise various additives and excipients well known in the art, including anti-caking agents, anti-foaming agents, anti-oxidants, binders, colorants, diluents, disintegrants, emulsifiers, encapsulating agents or formulations, enzymes, fats, flavour-enhancers, flavouring agents, gums, lubricants, polysaccharides, preservatives, proteins, solubilisers, solvents, stabilisers, sugar-derivatives, surfactants, sweetening agents, vitamins, waxes, and the like. Solvents which may be used are known to those skilled in the art and include e.g. ethanol, ethylene glycol, propylene glycol, glycerin, triacetin, diethyl phthalate and dimethyl phthalate. Encapsulants and gums include maltodextrin, gum arabic, alginates, gelatin, modified starch, and polysaccharides. Examples of additives, excipients, carriers, diluents or solvents for flavour or fragrance compounds may be found e.g. in "Perfume and Flavor Materials of Natural Origin", S. Arctander, Ed., Elizabeth, N.J., 1960; in "Perfume and Flavor Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

There now follows a series of non-limiting examples that serve to illustrate the invention.

EXAMPLES 1-4

Unless otherwise indicated, all sensory tests are triangle tests and are performed according to the guidelines in "Amtliche Sammlung von Untersuchungsverfahren nach § 35 LMBG (Lebensmittel-und Bedarfsgegenständegesetz)"; L 00.90 7, Untersuchung von Lebensmitteln, Sensorische Prüfverfahren, Dreiecksprüfung (Übernahme der gleichnahmigen Deutschen Norm DIN ISO 4120, Ausgabe Januar 1995), as follows:

The sensory panel is trained to evaluate the taste of aqueous solutions (4 ml each) of the following standard taste compounds by using a triangle test as described in the literature (Wieser and Belitz, Z. Lebensm. Unters. Forsch., 1975, 159, 65-72): sucrose (40 mmol/L) for sweet taste; citric acid (5 mmol/L) for sour taste; NaCl (12 mmol/L) for salt taste; caffeine (2 mmol/L) for bitter taste; and monosodium glutamate (MSG) (6 mmol/L) for umami taste. For kokumi taste, a solution of GSH (glutathione, 10 mmol/L) in diluted chicken broth concentrate (Goumet Bouillon Huhn, Maggi, Singen, Germany; 3 g/100 g bottled water (Evian®)) is prepared and compared to the taste of chicken broth with no glutathione added.

All sensory analyses are performed in a sensory panel room at 22-25° C. over three different sessions by a trained panel of 8 to 10 individuals.

For recording the taste profiles, samples are prepared as indicated in the examples below. Taste profiles of samples are determined in a triangle test in three different sessions. Panellists refrain from eating or drinking for at least 1 hour prior to the session. At the start of the session and before each trial, the subject rinsed with water and expectorated. The participants receive a set of two blanks and one taste sample. Liquid samples are swirled around in the mouth briefly and expectorated. Solid samples are chewed for 20 seconds and then expectorated. After indicating which glass vial shows a different taste profile and description of the distinction, the participant receives another trial set of two blanks and one taste sample. Each sample with additive is compared to two reference samples without additives. Kokumi intensity is rated according to a scale from 0 to 5 (with 5 most intensive). The additive is added to a consumable and the sample is homogenised. The samples are presented to the sensory panel directly after homogenisation. The sensory panel in all tests included 8 trained individuals.

The table below shows the tested compounds of formula I with the residues $R^1$-$R^4$ and X and Y indicated.

| Compound of formula I | $R^1$ | $R^2$ | $R^3$ | $R^4$ | X | Y |
|---|---|---|---|---|---|---|
| S-(α,β-dicarboxyethyl dimethylester) γ-L-glutamyl-L-cysteinyl-glycine | $CH_2$ | Gly | γ-glu | $CH_3$ | S | $CH(COOH)CH_2$ |
| S-(α,β-dicarboxyethyl diethylester) γ-L-glutamyl-L-cysteinyl-glycine | $CH_2$ | Gly | γ-glu | $CH_2CH_3$ | S | $CH(COOH)CH_2$ |
| S-(α,β-dicarboxyethyl dimethylester) γ-L-glutamyl-L-cysteine | $CH_2$ | OH | γ-glu | $CH_3$ | S | $CH(COOH)CH_2$ |
| S-(α,β-dicarboxyethyl diethylester) γ-L-glutamyl-L-cysteine | $CH_2$ | OH | γ-glu | $CH_2CH_3$ | S | $CH(COOH)CH_2$ |
| α-S-(α,γ-dicarboxypropyl dimethylester) γ-L-glutamyl-L-cysteine | $CH_2$ | OH | γ-glu | $CH_3$ | S | $CH(CH_2CH_2COOH)CH_2$ |
| α-S-(α,γ-dicarboxypropyl diethylester) γ-L-glutamyl-L-cysteine | $CH_2$ | OH | γ-glu | $CH_2CH_3$ | S | $CH(CH_2CH_2COOH)CH_2$ |
| α-S-(α,γ-dicarboxypropyl dimethylester) γ-L-glutamyl-L-cysteinyl-glycine | $CH_2$ | Gly | γ-glu | $CH_3$ | S | $CH(CH_2CH_2COOH)CH_2$ |
| α-S-(α,γ-dicarboxypropyl diethylester) γ-L-glutamyl-L-cysteinyl-glycine | $CH_2$ | Gly | γ-glu | $CH_2CH_3$ | S | $CH(CH_2CH_2COOH)CH_2$ |

Example 1

Sensory Effects of Compounds of Formula I in Chicken Broth

Sensory tests (triangle test) are performed at least twice for each compound using sensory panels of different individuals to confirm the results.

Chicken Broth is prepared by dilution of 3 g chicken broth concentrate (Gourmet Bouillon Huhn; Maggi, Singen, Germany) with 100 ml water (Evian). Additives are added as specified in table below.

The pH-value of all samples is adjusted to 6.5 using formic acid (0.1 mol/L) or sodium hydroxide (0.1 mol/L).) GSH is determined to have a kokumi intensity of 3.5.

The results of the tests are indicated in the table below. For each sample, kokumi intensity is rated and panelists are asked to describe sensory characteristics.

| Chicken broth samples | concentration of additive | Kokumi intensity (0-5) | Sensory descriptors |
|---|---|---|---|
| Negative control (without additives) | — | 2 | — |
| Positive control: NaCl | 30 mmol/L | 2 | increased salty taste |
| Positive control: MSG (mono sodium glutamate) | 10 mmol/L | 2 | Increased umami taste |
| GSH, reduced form [γ-Glu-Cys-Gly] | 10 mmol/L | 3.5 | Increased complexity and mouthfulness, more rich, more impact, punch |
| GSH, oxidized form (disulfide) | 10 mmol/L | 2.5 | slight increase of mouthfulness and complexity |
| S-(α,β-dicarboxyethyl dimethylester) γ-L-glutamyl-L-cysteinyl-glycine | 10 mmol/L | 3.5 | strong increase of mouthfulness and complexity, more rich, impact, punch; |
| S-(α,β-dicarboxyethyl diethylester) γ-L-glutamyl-L-cysteinyl-glycine | 10 mmol/L | 3.5 | Increase of mouthfulness and complexity, more rich, impact, punch |
| S-(α,β-dicarboxyethyl dipropylester) γ-L-glutamyl-L-cysteinyl-glycine | 10 mmol/L | — | bitter |
| S-(α,β-dicarboxyethyl dimethylester) γ-L-glutamyl-L-cysteine | 10 mmol/l | 4.5 | Strong increase of mouthfulness, more complex, long lasting |
| S-(α,β-dicarboxyethyl diethylester) γ-L-glutamyl-L-cysteine | 10 mmol/L | 4.5 | Strong increase of mouthfulness, more complex, long lasting |
| S-(α,β-dicarboxyethyl dipropylester) γ-L-glutamyl-L-cysteine | 10 mmol/L | — | bitter |

The panel rates the positive control with NaCl more salty than the negative control and the positive control with MSG as having the higher umami (taste of MSG) intensity, but no effect on mouthfulness and complexity of the taste profile is observed.

All tested compounds comprising methyl or ethyl esters increase the mouthfulness, complexity, and longlasting taste sensation of chicken broth. The most intense kokumi effect is found for the γ-L-glutamyl-L-cysteine-derivatives, which have an even more pronounced kokumi effect than GSH.

Example 2

Kokumi Compounds in Tomato Juice

Compounds as indicated in the table below are added to tomato juice (Albi, Germany) in the concentrations indicated below.

| Tomoatoe juice samples | Test results |
|---|---|
| Reference without additives | — |
| S-(α,β-dicarboxyethyl diethylester) γ-L-glutamyl-L-cysteinyl-glycine (1000 ppm) | Preferred, more intensive, well balanced and aromatic kokumi taste |
| S-(α,β-dicarboxyethyl diethylester) γ-L-glutamyl-L-cysteinyl-glycine (5000 ppm) | Preferred, more intensive, well balanced and aromatic kokumi taste |
| S-(α,β-dicarboxyethyl diethylester) γ-L-glutamyl-L-cysteine (1000 ppm) | Preferred, more intensive, well balanced and aromatic kokumi taste, S-(α,β-dicarboxyethyl diethylester) γ-L-glutamyl-L-cysteinyl-glycine (1000 ppm) |

S-(α,β-dicarboxyethyl diethylester) γ-L-glutamyl-L-cysteinyl-glycine (1000 ppm) is preferred by 6 out of 8 panelists, and is described as having a more intensive and well-balanced kokumi taste. This effect is increased with ascending concentrations.

S-(α,β-dicarboxyethyl diethylester) γ-L-glutamyl-L-cysteine (1000 ppm) shows an even more pronounced kokumi sensation and is preferred by all panelists.

Example 3

Kokumi Compounds in Cream Cheese

Compounds as indicated in the table below are added to Cream cheese (Philadelphia, Kraft) to a final concentration of 1000 ppm. The mixture is stirred until homogeneous. The results are listed in the table below.

| Cheese cream samples | Test results |
| --- | --- |
| Reference without additives | — |
| S-(α,β-dicarboxyethyl dimethylester) γ-L-glutamyl-L-cysteinyl-glycine | Preferred, more intensive, increased punch and mouthfulness, long lasting taste sensation |
| S-(α,β-dicarboxyethyl diethylester) γ-L-glutamyl-L-cysteinyl-glycine | Preferred, more intensive, increased punch and mouthfulness, long lasting taste sensation |

7 out of a panel of 8 find samples with additives different from reference sample and preferred. Both samples are described to possess more mouthfulness, richness, and kokumi-like complexity.

Example 4

Kokumi Compounds in Ketchup

Compounds as indicated in the table below are added to ketchup (Kraft) in a concentration of 2500 ppm.

| Ketchup samples | Test results |
| --- | --- |
| Reference without additives | — |
| S-(α,β-dicarboxyethyl diethylester) γ-L-glutamyl-L-cysteinyl-glycine | More meaty, bouillon-like, and intensified overall taste. |
| S-(α,β-dicarboxyethyl diethylester) γ-L-glutamyl-L-cysteine | More meaty, bouillon-like, and intensified overall taste. |

Samples with S-(α,β-dicarboxyethyl diethylester) γ-L-glutamyl-L-cysteinyl-glycine and S-(α,β-dicarboxyethyl diethylester) γ-L-glutamyl-L-cysteine are indicated by 7 out of 8 panelists to have a more meaty, bouillon-like, and intensified overall taste, the observed effect for S-(α,β-dicarboxyethyl diethylester) γ-L-glutamyl-L-cysteinyl-glycine compared to S-(α,β-dicarboxyethyl diethylester) γ-L-glutamyl-L-cysteine is lower.

Example 5

Synthesis of S-Carboxyalkyl Esters of Sulfur-Containing Peptides

The reaction between a thiol compound (glutathione (H-γ-Glu-Cys-Gly-OH), γ-glutamyl-cysteine (H-γ-Glu-Cys-OH), H-β-Asp-Cys-Gly-OH, β-L-Asp-Cys-OH), and an unsaturated carboxylic acid ester having at least one double bond (maleic acid dimethylester, maleic acid diethylester, glutaconic acid dimethylester, glutaconic acid diethylester, acrylic acid ethylester, 2-pentenoic acid ethylester, aconitic acid triethylester etc.) is performed according to the procedure reported by Morgan and Friedmann (*Biochemical Journal*, 32 (1938); 733-742) as follows:

The unsaturated ester compound (10 mmol) and the thiol compound (10 mmol) are dissolved in water (100 ml), the pH of the sample is adjusted to pH 7.4 with NaOH (1 mol/L) and the sample is incubated at 37° C. for 24 h.

After freeze-drying, the formed reaction products are purified by means of gel permeation chromatography using Sephadex G-10 (Amersham Bioscience, Uppsalla, Sweden) as stationary phase and water as mobile phase. The formed reaction products elute between 750 and 850 mL of mobile phase, the identity and purity is confirmed by means of LC-MS and NMR spectroscopy.

What is claimed is:
1. A flavourant compound according to the formula (I), or a salt thereof,

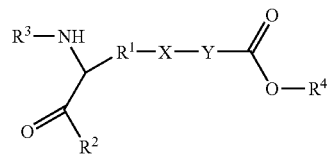

wherein:
$R^1$ is a residue selected from —$CH_2$—; —$CH_2CH_2$— or —$CH_2CH_2CH_2$—;
$R^2$ is a residue selected from —OH, —$C_1$-$C_5$ linear or branched alkoxy residue including —O—$CH_3$, —O—$CH_2$—$CH_3$, —O—$CH_2CH_2CH_3$, —O—CH($CH_3$)$CH_3$, —O—$CH_2CH(CH_3)_2$, —O—$CH_2$CH($CH_3$)($CH_2CH_3$), and —O—$CH_2CH_2CH(CH_3)_2$ and the residue of an amino acid selected from the group consisting of α-Ala, α-Gly, α-Val, α-Leu, α-Ile, α-Met, α-Pro, α-Phe, α-Trp, α-Ser, α-Thr, α-Asn, α-Gln, α-Tyr, α-Cys, α-Lys, α-Arg, α-His, α-Asp, α-Glu, β-Ala, and gamma amino butyric acid (GABA), and an uncommon amino acid including 4-hydroxyprolin, ε-N, N,N-trimethyllysine, 3-methylhistindine, 5-hydroxylysine, O-phosphoserine, gamma-carboxyglutamate, ε-N-acetyllysine, ω-N-methylarginine, N-acetylserine, N,N,N-trimethylalanine, N-formylmethionine;
$R^3$ is a residue selected from the group of a residue of γ-Glu (—CO—$CH_2$—$CH_2CH(NH_2)COOH$), and β-Asp (—CO—$CH_2$—CH($NH_2$)—COOH);
X is a residue selected from —S— or —O—; and
Y is a residue selected from: —$CH_2$—, —$CH_2CH_2$—, $CH_2CH_2CH_2$—, —CH(COO$R^4$)—, —C(COO $R^4$)$_2$—, —C($CH_2$COO $R^4$)$_2$—, —C($CH_2$COO $R^4$)(COO $R^4$)—, —C(CH(COO $R^4$)$_2$)(COO $R^4$)—, —CH($CH_2$COO $R^4$)—, —CH($CH_2CH_2$COO $R^4$)—, —CH($CH_2CH_2CH_2$COO $R^4$)—, —CH(CH(COO $R^4$)$_2$)—, —CH(CH(COO $R^4$)CH(COO $R^4$)$_2$)—, —CH($CH_2$CH(COO $R^4$)$_2$)—, —CH(CH(COO $R^4$)$CH_2$COO $R^4$)—, —$CH_2$—CH(COO $R^4$)—, —$CH_2$—C(COO $R^4$)$_2$—, —$CH_2$—C($CH_2$COO $R^4$)$_2$—, —$CH_2$—C($CH_2$COO $R^4$)(COO $R^4$)—, —$CH_2$—C(CH(COO $R^4$)$_2$)(COO $R^4$)—, —$CH_2$—CH($CH_2$COO $R^4$)—, —$CH_2$—CH($CH_2CH_2$COO $R^4$)—, —$CH_2$—CH($CH_2CH_2CH_2$COO $R^4$)—, —$CH_2$—CH(CH(COO $R^4$)$_2$)—, —$CH_2$—CH(CH(COO $R^4$)CH(COO $R^4$)$_2$)—, —$CH_2$—CH($CH_2$CH(COO $R^4$)$_2$)—, —$CH_2$—CH(CH(COO $R^4$)$CH_2$COO $R^4$)—, —CH(COO $R^4$)—$CH_2$—, —C(COO $R^4$)$_2$—$CH_2$—, —C($CH_2$COO $R^4$)$_2$—$CH_2$—, —C($CH_2$COO $R^4$)(COO $R^4$)—$CH_2$—, —C(CH(COO $R^4$)$_2$)(COO $R^4$)—$CH_2$—, —CH($CH_2$COO $R^4$)—$CH_2$—, —CH($CH_2CH_2$COO $R^4$)—$CH_2$—, —CH($CH_2CH_2CH_2$COO $R^4$)—$CH_2$—, —CH(CH(COO $R^4$)$_2$)—$CH_2$—, —CH(CH(COO $R^4$)CH(COO $R^4$)$_2$)—$CH_2$—, —CH($CH_2$CH(COO $R^4$)$_2$)—$CH_2$—, —CH(CH(COO $R^4$)$CH_2$COO $R^4$)—$CH_2$—; and
$R^4$ is a residue selected from a $C_1$-$C_5$ linear or branched alkyl residue including —$CH_3$, —$CH_2$—$CH_3$, —$CH_2CH_2CH_3$, —CH($CH_3$)$CH_3$, —$CH_2CH(CH_3)_2$, —$CH_2CH(CH_3)(CH_2CH_3)$, and —$CH_2CH_2CH(CH_3)_2$, and wherein, when more than two $R^4$ residues are present, at least one $R^4$ residue is a $C_1$-$C_5$ linear or branched alkyl residue and of the remaining $R^4$ residues, one or more may be H, and wherein, when one of the $R^4$ residues is a propyl, butyl or pentyl residue, then the other $R^4$ residues are selected from methyl or ethyl or H.

2. A flavourant compound according to claim 1 wherein two or more identical $R^4$ residues are present.

3. A flavourant compound according to claim 1 wherein $R^1$ is selected from —$CH_2$— and —$CH_2CH_2$.

4. A flavourant compound according to claim 1 wherein $R^1$ is —$CH_2$— and —$CH_2CH_2$.

5. A flavourant compound according to claim 1 wherein $R^3$ is γ-Glu.

6. A flavourant compound according to claim 1 wherein $R^4$ is selected from —$CH_3$, and —$CH_2$—$CH_3$.

7. A flavourant compound according to claim 1 wherein X is S.

8. A flavourant compound according to claim 1 wherein Y is selected from: —$CH_2$—, —CH(COO $R^4$)—, —CH(COO $R^4$)$CH_2$—, —CH(CH(COO $R^4$)$_2$)—, —$CH_2CH_2$—, —$CH_2CH_2$ $CH_2$—, and —CH($CH_2$COO $R^4$)$CH_2$.

9. A flavourant compound according to claim 1 wherein $R^3$ is γ-Glu, and $R^4$ is selected from —$CH_3$, and —$CH_2$—$CH_3$.

10. A flavourant compound according to claim 1 wherein $R^3$ is γ-Glu, and X is S.

11. A flavourant compound according to claim 1 wherein $R^3$ is γ-Glu, and Y is selected from: —$CH_2$—, —CH(COO $R^4$)—, —CH(COO $R^4$)$CH_2$—, —CH(CH(COO $R^4$)$_2$)—, —$CH_2CH_2$—, —$CH_2CH_2$ $CH_2$—, and —CH($CH_2$COO $R^4$)$CH_2$.

12. A flavourant compound according to claim 1 wherein $R^3$ is γ-Glu, $R^4$ is selected from —$CH_3$, and —$CH_2$—$CH_3$, X is S, and Y is selected from the group consisting of —$CH_2$—, —CH(COO $R^4$)—, —CH(COO $R^4$)$CH_2$—, —CH(CH(COO $R^4$)$_2$)—, —$CH_2CH_2$—, —$CH_2CH_2$ $CH_2$—, and —CH($CH_2$COO $R^4$)$CH_2$.

13. A flavourant compound according to claim 1 wherein more than two $R^4$ residues are present, and at least one $R^4$ residue is a $C_1$-$C_5$ linear or branched alkyl residue and of the remaining $R^4$ residue or residues, one or more is H.

14. A flavourant compound according to claim 1 wherein more than two $R^4$ residues are present, and at least one $R^4$ residue is a $C_1$-$C_5$ linear or branched alkyl residue and of the remaining $R^4$ residue or residues, two or more are H.

15. A method to form a flavourant compound according to claim 1.

16. A flavour composition comprising one or more compounds according to claim 1.

17. A consumable containing one or more flavourant compounds according to claim 1, in a concentration of 1 to 25,000 ppm (weight/weight).

18. A method for imparting a kokumi flavour to a consumable, comprising providing one or more flavourant compounds according to claim 1 to a consumable in a concentration sufficient to impart a kokumi flavour.

19. A method according to claim 18 wherein the flavourant compound is added in form of an unpurified enzymatic reaction mixture in which it was formed, in form of a crude extract of such a mixture, in form of a plant extract, in form of a plant isolate, or in a purified form.

* * * * *